United States Patent
Deng et al.

(10) Patent No.: US 7,122,110 B2
(45) Date of Patent: Oct. 17, 2006

(54) ELECTROCHEMICAL TEST SENSOR

(75) Inventors: Yingping Deng, Fishers, IN (US);
Sherry J. Jamison, Goshen, IN (US);
Andrew J. Edelbrock, Granger, IN (US)

(73) Assignee: Bayer HealthCare LLC, Tarrytown, NY (US)

(*) Notice: Subject to any disclaimer, the term of this patent is extended or adjusted under 35 U.S.C. 154(b) by 0 days.

(21) Appl. No.: 10/992,593

(22) Filed: Nov. 18, 2004

(65) Prior Publication Data
US 2006/0037870 A1    Feb. 23, 2006

Related U.S. Application Data

(63) Continuation of application No. 10/142,214, filed on May 10, 2002, now abandoned.

(60) Provisional application No. 60/292,005, filed on May 21, 2001.

(51) Int. Cl.
*G01N 27/327* (2006.01)
*B05D 3/00* (2006.01)

(52) U.S. Cl. .............. 205/777.5; 204/403.14; 204/403.01; 204/416; 427/2.13

(58) Field of Classification Search .......... 204/403.04, 204/403.09, 403.1, 403.11, 403.14, 416–418, 204/403.01; 427/2.13, 2.12; 205/777.5, 205/778, 789, 789.5, 787
See application file for complete search history.

(56) References Cited

U.S. PATENT DOCUMENTS

| 5,759,364 A | * | 6/1998 | Charlton et al. ....... 204/403.14 |
| 6,531,040 B1 | * | 3/2003 | Musho et al. ............... 204/401 |
| 6,841,052 B1 | * | 1/2005 | Musho et al. ............... 204/401 |

FOREIGN PATENT DOCUMENTS

| EP | 0 732 406 | 9/1996 |
| EP | 0 735 363 | 10/1996 |
| EP | 1 074 832 | 2/2001 |

* cited by examiner

*Primary Examiner*—Alex Noguerola

(57) ABSTRACT

Disclosed is an improved electrochemical sensor for the detection of an analyte in a fluid test sample. The electrochemical sensor is of the type in which the fluid test sample is drawn into a capillary space and the improvement to the sensor involves an arrangement where a portion of the sensor's counter electrode is placed on the edge of the capillary space in a relationship to the sensor's working electrode such that if the capillary space is not completely filled there will be generated only a very weak current. When the sensor is connected to a properly programmed current detector, the weak current caused by the underfilling of the capillary space will be detected as an error and will notify the user of the sensor that the test should not be continued.

21 Claims, 2 Drawing Sheets

ELECTROCHEMICAL TEST SENSOR

This is a continuation application of U.S. Ser. No. 10/142,214, filed May 10, 2002, now abandoned, which claims benefit of provisional application 60/292,005, filed May 21, 2001.

BACKGROUND OF THE INVENTION

The present invention relates to an electrochemical biosensor which can be used for the determination of a specific component (analyte) in a fluid test sample. Electrochemical biosensors of the type under consideration are disclosed in U.S. Pat. Nos. 5,120,420 and 5,264,103. These devices have an insulating base upon which carbon electrodes are printed and are then covered with a reagent layer comprising a hydrophilic polymer in combination with an oxidoreductase specific for the analyte. These devices typically involve a base and a cover which are separated by a generally U-shaped piece as a spacer element, so that when the base and cover are mated there is created a capillary space containing the electrodes covered by the reagent layer. In an alternative structure, the cover is embossed so as to form the capillary space when it is mated with the base thereby eliminating the need for the spacer element. A hydrophilic polymer, e.g. carboxymethyl cellulose or poly (ethylene oxide) is used to facilitate the drawing of the aqueous test fluid into the capillary space.

In either embodiment, working and counter electrodes are screen printed onto the base so that an electrochemically created current can flow when these electrodes are electrically connected and a potential is created between them. Touching the opening in the end of the sensor to a drop of test fluid such as blood results in the fluid being drawn into the capillary space, so that it covers the reaction layer on the surface of the electrode. An enzymatic reaction between the oxidoreductase and the analyte creates a flow of electrons which are carried to the working electrode by a mediator such as ferricyanide and flow through the working electrode to a meter which measures the magnitude of the current flow. The counter electrode serves dual purposes. First, it provides a fixed potential against which the working electrode is controlled. Second, for a two electrode system, such as that depicted in FIGS. 1 and 2, the counter electrode is used to complete the electrical circuit. In this mode, each electron that is transferred to the working electrode is returned to the test fluid at the counter electrode side of the cell. The device's software is programmed to correlate the magnitude of this flow with the concentration of analyte in the test sample. In order for this current to flow, a complete circuit is formed by covering both electrodes with the conductive test sample fluid and applying a potential therebetween.

A problem which is sometimes associated with this type of sensor occurs when an insufficient amount of blood is applied to the opening, so that the counter and working electrodes are not completely covered with the sample. This results in an incomplete current flowing across the electrodes. Since the amount of analyte detected is directly proportional to the current flowing through the detection meter, failure to completely cover the sensor's electrodes can result in an artificially low reading of the sample's analyte concentration. One technique for dealing with this under filling problem is claimed in U.S. Pat. No. 5,628,890 which involves a mechanism for preventing any response from being detected when the sample volume is too low to provide an accurate reading. This design involves a strip comprising an elongated electrode support defining a sample transfer path for directional flow of the sample from a sample application point. A working electrode is placed in the sample transfer path and a counter or reference electrode down stream from the working electrode in the sample transfer path. Failure of the test sample to totally cover the working electrode will result in no response from the reading mechanism due to the absence of a closed circuit through which current can flow.

In co-pending application Ser. No. 09/731,943 there is disclosed an electrochemical sensor of the type described above in which a small sub-element of the non-working electrode is positioned upstream from the working electrode, so that when there is insufficient flow of electrical current through the detector to constitute a valid test for the concentration of analyte in the fluid test sample, the pre-programmed detector causes the emission of an error signal to alert the user of the device that the test result should be disregarded. This is achievable because there is generated an altered current profile in the event the capillary space of the sensor is underfilled. It has been discovered, however, that the use of the sub-element of the counter electrode, sometimes referred to as the trigger electrode, can result in a delayed response in terms of activating the system which delay adds unnecessary time to the duration of the analyte assay. This may be due to the lower initial current being generated by the partially covered working electrode and the small trigger electrode in underfilled sensors.

SUMMARY OF THE INVENTION

The present invention is an electrochemical sensor for detecting the concentration of analyte, e.g. glucose, in a fluid test sample such as blood. The sensor comprises:
1) a base having a front edge which provides a flow path for the fluid test sample which base has on its upper surface a counter electrode and a working electrode in electrical communication with a detector of electrical current,
2) a reaction layer on the surface of at least the working electrode which contains an enzyme reactive with the analyte to provide electrons which are transferred to the working electrode, and
3) a cover which when mated with the base forms a capillary space with an opening for the introduction of fluid test sample into the space and which capillary space encloses the flow path for the fluid test sample on which the counter and working electrodes are contained. These electrodes are situated on the base in relation to the opening, so that a major portion of the counter electrode is located downstream of the opening from the working electrode. The counter electrode has a sub-element located upstream from the working electrode and flush with the front edge of the base, so that when electrical communication between only the sub-element of the counter electrode and working electrode due to incomplete filling of the capillary space by the fluid test sample occurs, there is insufficient flow of electrical current through the detector to constitute a valid test for the concentration of analyte in the fluid test sample. In the event of such insufficient flow of electrical current, the detector, which is pre-programmed to do so, gives an error signal to notify the user that the test has failed and that it should be repeated.

DESCRIPTION OF THE INVENTION

Figure 1:
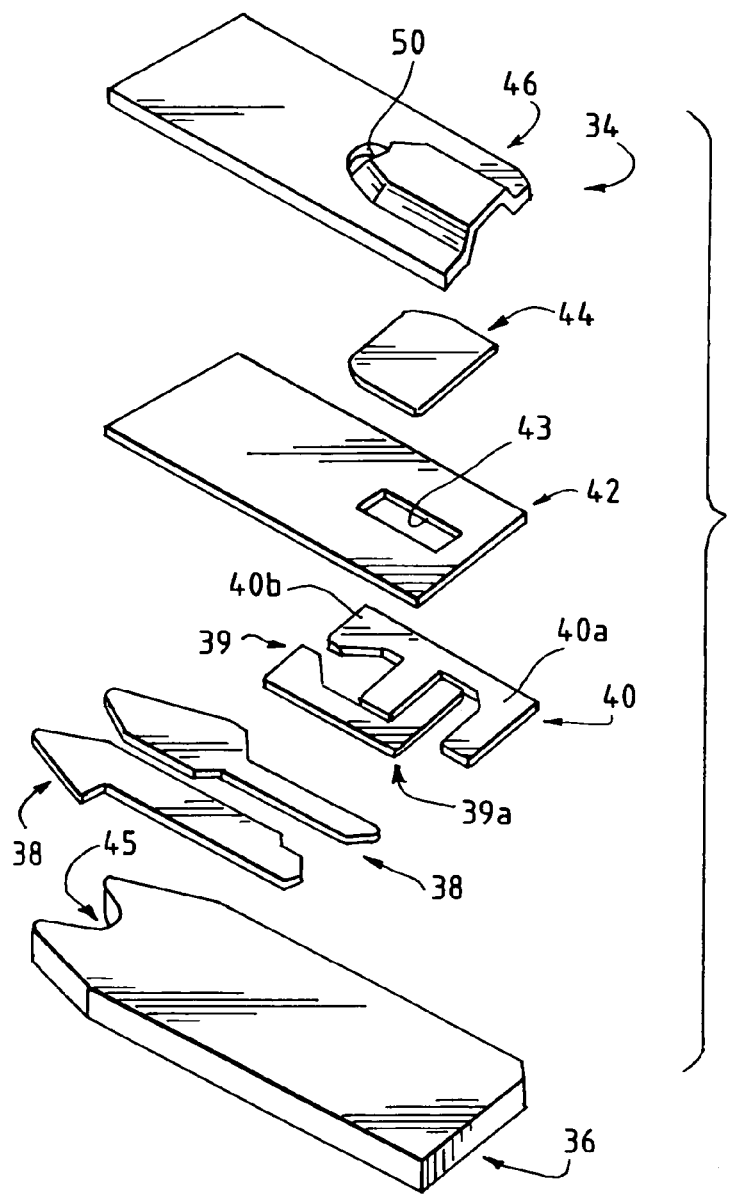
FIG. 1 represents an exploded view of a sensor of the present invention.

The construction of the electrochemical sensor with which the present invention is concerned is illustrated by FIG. 1. The sensor 34 is made up of insulating base 36 upon which is printed in sequence (typically by screen printing techniques) an electrical conductor pattern 38, an electrode pattern (39 and 40), an insulating (dielectric) pattern 42 and a reaction layer 44. The function of the reaction layer is to convert glucose, or other analyte in the fluid test sample, stoichiometrically into a chemical species which is electrochemically measurable, in terms of the electrical current it produces, by the components of the electrode pattern. The reaction layer typically contains an enzyme which reacts with the analyte to produce mobile electrons and an electron acceptor such as ferricyanide to carry the mobile electrons to the surface of the working electrode. The enzyme in the reaction layer can be combined with a hydrophilic polymer such as carboxymethylcellulose or poly(ethylene oxide). The two parts, 39 and 40, of the electrode print provide the working 39 and counter 40 electrodes necessary for the electrochemical determination of the analyte which is the crux of the present invention. The working and counter electrodes are configured in a manner such that the major portion of the counter electrode is located downstream (in terms of the direction of fluid flow along the flow path) from the forward position of the working electrode 39a. This configuration offers the advantage of allowing the test fluid to completely cover the exposed portion of the working electrode for all cases in which an undetected partial fill has occurred. However, sub-element 40a of the counter electrode is positioned upstream from working electrode upper element 39a, so that when an inadequate amount of fluid test sample to completely cover the working electrode enters the capillary space, there will be formed an electrical connection between counter electrode sub-element 40a and the exposed portion of the working electrode upper part 39a due to the conductivity of the fluid sample, e.g. blood. By programming the current detector to give an error signal when the current it receives is below a certain pre-determined level, the sensor system can be made to actively advise the user that insufficient blood has entered the sensor's cavity and that another test for analyte concentration should be conducted. The system is designed to give an error signal in the case of a short fill by generating a current profile when the capillary space is underfilled which is different from that which is obtained when there is complete filling of the capillary space. However, it was found that this design, requires more time than is desirable to activate the assay. This delay may be caused by a lower initial current being generated by the electrodes. It has now been discovered that this delay can be shortened or eliminated by printing the sub-element of the counter electrode all the way to the tip of the sensor's base plate to cause it to be flush therewith. This is preferably achieved by printing the sub-element onto the base and then cutting the base through the print to leave the sub-element flush with the front edge created by the cutting step. Sensor's of this design trip immediately upon entry of the fluid test sample into the capillary space and the error detection feature will not affect the final glucose readings. While we do not intend to be limited by any particular theory of how the present operates, this is believed to be the result of a decreased cell resistance and an increased rest potential of the redox couple in the cell containing a trigger electrode.

In one embodiment of the manufacture of the sensor of the present invention there are carried out four printing passes on the electrode base (36 in FIG. 1). The first pass lays down the contact leads 38 which typically comprise a silver/carbon ink. The second pass lays down the working and counter electrode 39 and 40 which typically comprise carbon with the third pass applying the dielectric layer 42 and the fourth printing the reaction layer 44. A plurality of base members are typically prepared by printing the above described layers on to a sheet of base stock which is typically made of polycarbonate. The lid 46 is also prepared by embossing a plurality of lids into a sheet of polycarbonate lid stock to provide the necessary concave spaces whereupon holes are punched into the polycarbonate sheet for registration and tracking. In order to assemble the lid stock to the base stock, a ribbon of lid stock is passed through a special laminator where it is registered and then combined with a strip of base stock under heat and pressure to form a bond between the base stock and an adhesive on the underside of the lid stock. In order to singulate individual sensors from the laminate ribbon, the laminate is passed through punching equipment in which individual sensors are punched from the array. So long as the sub-element of the counter electrode is printed up to or overlapping the plane from which the front edge of the sensor is punched, the object of this invention, which is to provide a sensor in which the sub-element is flush with the front edge, is accomplished.

While the particular dimensions of the electrodes are not critical, the area of the sub-element of the counter electrode is typically less than that of the working electrode. This element is made as small as possible in view of the restraints of the screen printing process and the area which is exposed to the fluid test sample can be made even smaller by printing the dielectric layer 42, so that only a very small portion (2% to 7% of the area of the working electrode) is exposed to provide the sub-element of the counter electrode, i.e. the trigger electrode. In order to achieve the advantages of the present invention, the entire leading edge of the sub-element of the counter electrode is preferably made flush with the front edge of the base 36. It is also contemplated that reaction layer 44 can be removed from contact with sub-element 40a of the counter electrode. This is accomplished by producing a screen that does not print reagent ink over the counter electrode sub-element 40a and serves the purpose of starving the sub-element for reagent, thereby not allowing it to function as a proper counter electrode. This is preferred, so that an error condition is achieved in the case of failure of the test fluid to contact the bulk of the counter electrode 40. While sub-element 40a is depicted as being physically connected to, and therefore part of, the counter electrode 40, such physical connection is not critical. The sub-element can be physically disconnected from the rest of the counter electrode as long as it is provided with its own connector and the sensor is equipped with a third contact to the connector.

The two parts 39 and 40 of the printed electrodes provide the working and counter electrodes necessary for the electrochemical determination of the analyte. The electrode ink, which is about 14μ (0.00055") thick, typically contains electrochemically active carbon. Components of the conductor ink are preferably a mixture of carbon and silver which is chosen to provide a path of low chemical resistance between the electrodes and the detector with which they are in operative connection via contact with the conductive pattern at the fish-tail end 45 of the sensor. The counter electrode can be comprised of silver/silver chloride in which case it will function more like a reference electrode. The function of the dielectric pattern 42 is to insulate the electrodes from the fluid test sample except in a defined area near the center of the electrode patterns to enhance the reproducibility of the detector reading. A defined area is important in this type of electrochemical determination because the measured current is dependent both on the concentration of the analyte and the area of the reaction layer which is exposed to the analyte containing test sample. A typical dielectric layer 42 comprises a UV cured acrylate modified polymethane which is about 10μ (0.00041") thick. In one embodiment of the present invention, the exposed electrode sub-element is made in two parts, the first of which is a standard window formed by the ink and a slot in the dielectric layer and the second from the exposed width of the ink along the front edge of the sensor. The dielectric slot can be from about 0.006 to 0.014 (0.010 preferred) inches wide and connects the window 43 with the front edge of the dielectric layer 42. The exposed ink varies from 0.010 to 0.016 inches and is dependent on screenprinting and punching tolerances. The second exposed sub-element, described hereafter, is better controlled. In the second embodiment, which is preferred, the length and thickness of the print are 0.200 and 0.0005 respectively and are easily controlled during the printing and excising of the sensor. In this version, only the front punched feature of the sensor forms the sub-element and there is very little variation between lots. The lid 46, which provides a concave space, is punctured to provide an air vent 50 and joined to the base 36 in a sealing operation. The method of joining the lid and base is more fully described in U.S. Pat. No. 5,798,031.

The construction of the sensor according to the present invention is accomplished according to the following general example:

EXAMPLE I

Figure 2:
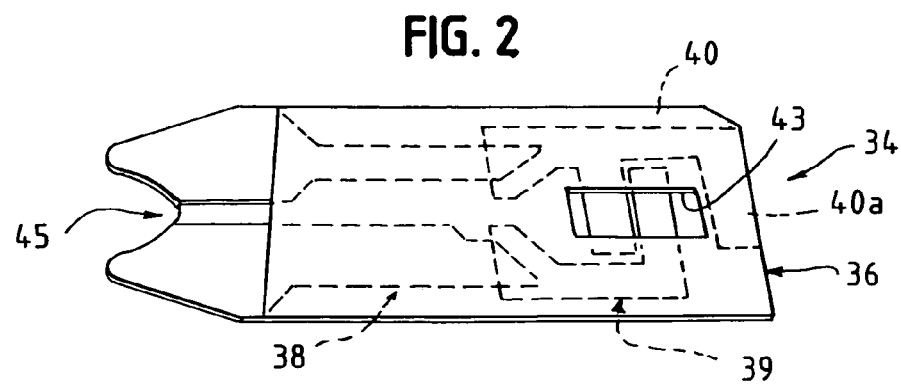
FIG. 2 represents the sensor's base and those elements of the sensor which are applied directly to the base.

The base stock, typically of polycarbonate, is printed with various inks to form the electrodes 39 and 40 and then overcoated with a dielectric layer 42 in a predetermined pattern designed to leave a desired surface of the electrode exposed to contact by the fluid test sample as it enters the space formed by the mating of lid 46 and base 36. The particular configuration of the dielectric layer 42 is depicted in FIG. 1, in which opening 43 leaves the reagent layer in electrical communication with the electrodes 39 and 40, is designed to define the extent to which all of the conductive elements (working, counter and sub-element electrodes) are exposed to the test fluid. Along with the printed conductive features, the dielectric layer defines the size of each of these elements. The electrodes are preferably printed so that the conductive and dielectric layers are close to 90 degrees to each other. This helps in the tolerance stack up for building the sensor because it reduces the registration issues. The sensor base of the present invention is also illustrated in FIG. 2 in which all elements on the base are shown on the same plane. The sensor's base 36 has conductive element 38 on its surface which is in turn overcoated with working electrode 39 and reference electrode 40. Dielectric layer 42 is not shown but instead the opening 43 in this layer is shown to illustrate the portions of the working electrode 39 and reference electrode 40 which are exposed by the opening. The sub-element of the counter electrode which is in electrical communication with the larger portion, designated as 40b, functions to provide an electrical conduction path with the working electrode such that the test fluid can be detected as having reached the working electrode. If the test fluid fails to fill the sensor cavity and contact the major portion of the counter electrode, an error condition will be detected and communicated to the user of the device. This can be accomplished by algorithmically programming the meter to detect an underfill by measuring the current at a definite time period, after the test fluid has electrically connected the sub-element of the counter electrode with the working electrode. The ratio of the currents for the two measurements is used to determine if the sensor has filled properly.

The present invention introduces the advantage of providing an electrochemical sensor in which the counter and working electrodes can be configured so that in the event of a short fill, the result will be affirmative as opposed to a neutral response, i.e. a failure of the detector to give any signal. Thus, when the amount of test fluid which enters the capillary space is sufficient to cover the sub-element of the counter electrode 40a, or 40b in the preferred embodiment, and that portion of the working electrode 39a which lies upstream from the main portion of the counter electrode 40, the detector will sense the values of error checking parameters derived from multiple current measurements exceeding their tolerance limits if the working electrode is not completely covered with the test fluid. The detector can be connected with the reading means to provide an error signal which will alert the user to the occurrence of a sort fill. The means of error checking are accomplished by algorithmically programming the meter to detect the short fill by measuring the current at a definite time period after the test fluid has electrically connected the sub-element of the counter electrode with the working electrode. The ratio of the currents for the measurements is used to determine if the sensor has filled properly. Thus, a short fill is determined by employing the following steps:

a) making multiple current measurements at different time periods when a driving potential is applied between the electrodes;

b) converting the multiple current measurements into error checking parameters; and c) checking the values of the error checking parameters against their corresponding tolerance limits to determine if a short fill has occurred.

For example, in a sensor system which applied a 0.4 V potential for 10 seconds after a blood sample is applied (known as the burn-off period), opens the circuit (OV potential) for 10 seconds (known as the wait period) and then applies a 0.4 V potential during the 10 second read period; the steps are carried out as follows:

Referring to Step A in the above paragraph, three current measurements are made during the test sequence: 1) at the end of the burn-off period denoted as $I_{r10}$; 2) at the 5 second during the read period denoted as $I_{r5}$; and 3) at the end of the read period denoted as $I_{r10}$.

Then in Step B, two parameters are determined from the three current measurements. These two parameters are used to determine if the sensor's capillary space has filled properly. The first parameter is the Decay factor, which describes the shape of current time course. The second parameter is the Read-to-Burn ratio that characterizes the magnitude of initial current in relation to the final current. The decay factor, k, is defined as:

$$k = \frac{\ln(I_{r5}) - \ln(I_{r10})}{\ln(10) - \ln(5)} \quad \text{Eq. 1}$$

Note: k characterizes how the current decays in a general current-glucose relationship $I = c \cdot G \cdot t^{-k}$, where I is the current, c is a constant, G is the glucose concentration, and t is the time.

The Read-to-Burn ratio, R/B is defined as:

$$R/B = I_{r10}/I_{b10} \quad \text{Eq. 2}$$

In Step C, the values of these two parameters are checked against their tolerance limits to determine if a short fill occurred. The tolerance limits are not constant. They change as glucose level changes. The tolerance-limit checking is described as Conditions 1 and 2 below. The criteria for a short fill are either Condition 1 or Condition 2 is true.

Condition 1 (Decay Factor Checking):

if $|k - (a_{k1} + b_{k1} \cdot G)| > w_k$ is true when $G \leq d_{k1}$, or if $|k - (a_{k2} + b_{k2} \cdot G)| > w_k$ is true when $d_{k1} < G \leq d_{k2}$, or if $|k - (a_{k3} + b_{k3} \cdot G)| > w_k$ is tue when $G > d_{k2}$    Eq. 3 where $a_{k1}$, $a_{k2}$, $a_{k3}$, $b_{k1}$, $b_{k2}$, $b_{k3}$, $w_k$, $d_{k1}$, $d_{k2}$, and $d_{k3}$ are predetermined constants, G is the glucose measurement.

Condition 2 (R/B Ratio Checking):

if $|R/B - (a_{c1} + b_{c1} \cdot G)| > w_c$ is true when $G \leq d_c$, or if $|R/B - (a_{c2} + b_{c2} \cdot G)| > w_c$ is true when $G > d_c$    Eq. 4 where $a_{c1}$, $a_{c2}$, $b_{c1}$, $b_{c2}$, $w_c$, and $d_c$ are predetermined constants, G is the glucose measurement.

The constants $a_k$'s, $b_k$'s, $d_k$'s and wk in Eq. 3 are predetermined experimentally:

Tests a large number of sensors at various glucose levels, G.

Calculates the decay factor, k, of each sensor from their $I_{b5}$ and $I_{b10}$ currents.

Plots all the data points in a k vs. G chart.

Fits a 3-piece piecewise-linear line to the data points, in the k vs. G chart. These three pieces are $a_{k1} + b_{k1} \times G$ for $G \leq d_{k1}$; $a_{k2} + b_{k2} \times G$ for $G > d_{k1}$ and $\leq d_{k2}$; and $a_{k3} + b_{k3} \times G$ for $G > d_{k2}$ Add a tolerance width of $\pm w_k$ to the three lines so that the band between the $-w_k$ and $+w_k$ is wide enough to enclose all the normal data points in the chart.

The constants $a_c$'s, $b_c$'s, $d_c$ and $w_c$ in Eq. 4 are also predetermined experimentally in the same way, on a R/B vs. G chart.

A sample calculation is as follows:

Step A—Make three current measurements of a sensor:

$I_{b10} = 505.1$ nA, $I_{r5} = 656.5$ nA, and $I_{r10} = 561.8$ nA.

Step B—Determine the value of the decay factor k and R/B Ratio:

The decay factor and read-to-burn ratio were calculated from the current measurements:

Decay Factor $$k = \frac{\ln(I_{r5}) - \ln(I_{r10})}{\ln(10) - \ln(5)} = \frac{\ln(656.5) - \ln(561.8)}{\ln(10) - \ln(5)} = 0.225$$

Read-to-Burn Ratio $R/B = I_{r10}/I_{b10} = 561.8/505.1 = 1.11$

Step C—Check against the tolerance limits:

The constants used in this example were:

$a_{k1} = 0.36$, $b_{k1} = -0.0002$ dL/mg, $w_k = 0.13$, and $d_{k1} = 100$ mg/dL The glucose reading from the sensor system is 22.9 mg/dL.

Condition 1 was true because of the first line in Eq. 3 was true.

if $|k - (a_{k1} + b_{k1} \cdot G)| > w_k$ is true when $G \leq d_{k1}$ $\Rightarrow$ $|0.225 - (0.36 - 0.0002 \cdot 22.9)| = 0.1304 > 0.13$ is true when $G = 22.9 \leq d_{k1} = 100$ No further check on Condition 2 was needed in this example, because Condition 1 was already true.

Therefore, this sensor was determined as a short fill.

Sensors were fabricated as described above with the sub-element of the counter electrode, who's surface area accounted for about 11% of the counter electrode's entire surface area and 13% of the surface area of the working electrode. The sub-element was printed over the prospective front edge of the base, so that when the completed sensor was punched out of the polycarbonate sheet, the leading edge of the sub-element was flush with the front edge of the sensor's base. The sensor was tested as follows: A portion of sample fluid was applied to the sensor which was insufficient to fill the entire capillary space but covered the sub-element of the counter electrode and a portion of the working electrode such that the sensor was under filled. The meter will detect the short fill based on the algorithm with the two parameters described above. If those two parameters do not meet the criteria listed above, an error message will be displayed. If the sample fluid applied to the sensor is sufficient to fill the entire capillary space, a normal glucose result will be displayed.

Figure 3:
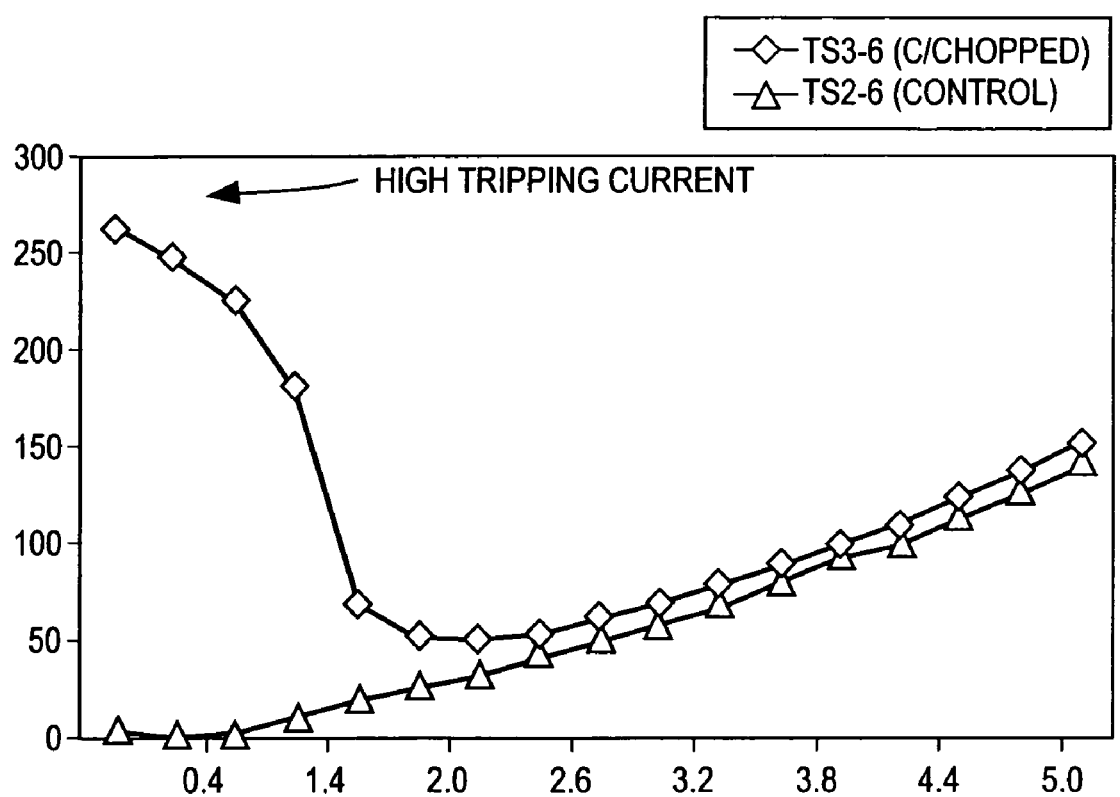
FIG. 3 represents initial current measured on under filled sensors with a control trigger having exposed surface area on the top of the base.

Sensors of the present invention TS3-6 (with a chopped trigger electrode on the front edge but no window on the surface of the base), and TS2-3, a control sensor with the sub-element printed so that there is a 450 μm gap between its leading edge and the front edge of the sensor's base. FIG. 3 is a graphical representation of the initial current of these under-filled sensors as a function of time from the time the blood sample was introduced into the sensor's capillary space. From FIG. 3 it can be determined that the initial current generated by the cell containing the chopped sub-element of this invention (TS3-6) and the working electrode is much larger than the control (TS2-3) and they are usually above the threshold predetermined in the meter. With the TS3-6 design, under-filled sensors typically tripped immediately or within 3 to 5 seconds after the sample fluid was applied. With the TS2-3 design, however, some of the sensors required more than a minute to trip.

The method of making the TS3-6 sensor forms the counter electrode sub-element by cutting through a sensor sub-element which is totally covered with ink. With this invention, the registration of printing the reaction layer to avoid its coming too close to the sub-element is not critical.

The invention claimed is:

1. An electrochemical test sensor for detecting the concentration of an analyte in a fluid test sample, the test sensor comprising:
   (1) a non-conductive base which provides a flow path for the fluid test sample, the base having a front edge, and a counter electrode and a working electrode on an upper surface thereof, the counter and working electrodes being adapted to be in electrical communication with a detector of electrical current;
   (2) a reaction layer on at least the surface of the working electrode the reaction layer comprising an enzyme which reacts with the analyte to produce electrons which are transferred to the working electrode; and
   (3) a cover coupled with the base and forming a capillary space with an opening for the introduction of fluid test sample thereto, the space containing a flow path for the fluid test sample, a major portion of the counter electrode being located downstream relative to the opening and at least a portion of the working electrode, and wherein a sub-element of the counter electrode is located upstream from the working electrode such that when electrochemical communication occurs between only the sub-element of the counter electrode and the working electrode there is insufficient flow of electrical current through the detector to constitute a valid test for determining the concentration of the analyte in the fluid test sample, the sub-element of the counter electrode being located on the upper surface of the base and being flush with the front edge of the base.

2. The electrochemical sensor of claim 1 further including a dielectric layer being located over the working electrode and counter electrode, the reaction layer being located over the dielectric layer, the dielectric layer forming at least one opening to expose the working and counter electrodes to the reaction layer, the area of the sub-element of the counter electrode that is exposed being 2% to 7% of the area of the working electrode that is exposed.

3. The electrochemical sensor of claim 2 wherein the sub-element of the counter electrode is not in contact with the reaction layer.

4. The electrochemical sensor of claim 1 wherein the sub-element is physically disconnected from the rest of the counter electrode, the sub-element being provided with its own connector that is adapted to contact with the detector.

5. The electrochemical sensor of claim 1 wherein the cover has a concave portion, the concave portion forming the capillary space when the cover is coupled with the base.

6. The electrochemical sensor of claim 1 further including a spacer element with a U shaped indentation, the U shaped indentation being located between the cover and the base and forming the capillary space.

7. A method for the production of a base member for an electrochemical test sensor for detecting the concentration of an analyte in a fluid test sample, the method comprising the acts of:
   a) providing an insulating base material in the form of a sheet, the sheet being adapted to form a plurality of bases, each of the plurality of bases having a front edge;
   b) screen printing an electrically conductive pattern onto the insulating base material;
   c) screen printing a plurality of working electrodes and a plurality of counter electrodes onto the conductive pattern so that a respective main portion of the plurality counter electrodes lies further from the front edge of a respective base than the working electrode and a respective sub-element of the plurality of counter electrodes overlaps the front edge of the respective base; and
   d) forming the plurality of bases from the sheet of insulating base material in a pattern such that the respective sub-elements of the plurality of counter electrodes are flush with the respective front edges of the plurality of bases.

8. An electrochemical test sensor adapted to assist in determining the concentration of an analyte in a fluid test sample, the test sensor comprising:
   a base that assists in forming an opening for introducing the fluid test sample, the base having a front edge;
   a working electrode being coupled to the base;
   a counter electrode being coupled to the base, the counter electrode and the working electrode being adapted to be in electrical communication with a detector of electrical current, a portion of the counter electrode being located downstream relative to the opening and at least a portion of the working electrode; and
   a sub-element being coupled to the base, the sub-element being located on the upper surface of the base and being flush with the front edge of the base, the sub-element being located upstream relative to the working electrode such that when electrical communication occurs between only the sub-element and the working electrode there is insufficient flow of electrical current through the detector to determine the concentration of the analyte in the fluid test sample.

9. The sensor of claim 8 further comprising a cover adapted to be coupled to the base to form a capillary space, the capillary space having an opening for introducing the fluid test sample therein, the capillary space forming a flow path for the fluid test sample, the working electrode and the counter electrode being situated in the flow path.

10. The sensor of claim 9 wherein the cover has a concave portion, the concave portion forming the capillary space when the cover is coupled with the base.

11. The sensor of claim 9 further including a spacer element with a U shaped indentation, the U shaped indentation being located between the cover and the base and forming the capillary space.

12. The sensor of claim 8 further comprising a reaction layer located on the surface of at least the working electrode, the reaction layer comprising an enzyme adapted to react with the analyte to produce electrons, the electrons being adapted to be transferred to the working electrode.

13. The sensor of claim 8, wherein the sub-element is physically disconnected from the counter electrode.

14. The sensor of claim 8 further including an enzyme that is adapted to react with the analyte, the enzyme being located on a surface of the working electrode.

15. A method of determining whether a sufficient quantity of a fluid test sample has been introduced to an electrochemical test sensor, the method comprising the acts of:
   providing the electrochemical test sensor adapted to assist in determining the concentration of an analyte in a fluid test sample, the sensor comprising a base, a working electrode, a counter electrode and a sub-element, the base assisting in forming an opening for introducing the fluid test sample, the base having a front edge, the working electrode being coupled to the base, the counter electrode being coupled to the base, a portion of the counter electrode being located downstream relative to the opening and at least a portion of the working electrode, the sub-element being coupled to the base, the sub-element being located on the upper surface of the base and being flush with the front edge of the base, the sub-element being located upstream relative to the working electrode such that when electrical communication occurs between only the sub-element and the working electrode there is insufficient flow of electrical current through the detector to determine the concentration of the analyte in the fluid test sample;

introducing the fluid test sample to the test sensor; and determining whether a sufficient quantity of the fluid test sample has been introduced and, if not, notifying a user that an insufficient quantity of the fluid test sample has been introduced.

16. The method of claim 15 wherein the test sensor further comprises a cover adapted to be coupled to the base to form a capillary space, the capillary space having an opening for introducing the fluid test sample therein, the capillary space forming a flow path for the fluid test sample, the working electrode and the counter electrode being situated in the flow path.

17. The method of claim 16 wherein the cover has a concave portion, the concave portion forming the capillary space when the cover is coupled with the base.

18. The method of claim 16 further including a spacer element with a U shaped indentation, the U shaped indentation located between the cover and the base and forming the capillary space.

19. The method of claim 15, wherein the test sensor further comprises a reaction layer located on the surface of at least the working electrode, the reaction layer comprising an enzyme adapted to react with the analyte to produce electrons, the electrons being adapted to be transferred to the working electrode.

20. The method of claim 15, wherein the sub-element is physically disconnected from the counter electrode.

21. The method of claim 15 further including an enzyme that is adapted to react with the analyte, the enzyme being located on a surface of the working electrode.

* * * * *